United States Patent [19]

McAleer et al.

[11] 4,242,457
[45] Dec. 30, 1980

[54] AUTOMATED VIRUS HARVESTING

[75] Inventors: William J. McAleer, Ambler; William M. Hurni, North Wales, both of Pa.

[73] Assignee: Merck & Co., Inc., Rahway, N.J.

[21] Appl. No.: 13,494

[22] Filed: Feb. 21, 1979

Related U.S. Application Data

[63] Continuation-in-part of Ser. No. 802,846, Jun. 2, 1977, abandoned.

[51] Int. Cl.³ .............................................. C12N 7/00
[52] U.S. Cl. .................................. 435/235; 435/239; 435/286; 435/289
[58] Field of Search ............... 435/235, 239, 284, 286, 435/289

[56] References Cited

U.S. PATENT DOCUMENTS

| | | | |
|---|---|---|---|
| 3,586,605 | 6/1971 | Hosler | 435/3 |
| 3,769,176 | 10/1973 | Hise et al. | 435/315 |
| 3,788,952 | 1/1974 | Iida et al. | 435/289 |
| 3,926,738 | 12/1975 | Wilson et al. | 435/290 |

Primary Examiner—Robert J. Warden
Attorney, Agent, or Firm—Donald J. Perrella; Julian S. Levitt

[57] ABSTRACT

Automated means are provided to harvest virus at a time when the yield is optimized and store the harvest with minimum loss thereby eliminating difficulties when the optimum yield time does not fall within normal working hours, enhancing sterility by limiting human contact and enhancing stability of the product.

6 Claims, 2 Drawing Figures

AUTOMATED VIRUS HARVESTING

RELATED APPLICATION

This application is a continuation-in-part of our co-pending U.S. patent application Ser. No. 802,846 filed June 2, 1977 now abandoned.

BACKGROUND OF THE INVENTION

It is known that optimal viral yields are obtained by harvesting a virus when the viral titer is at a maximum. It frequently happens, however, that the maximum viral titer occurs outside of normal working hours, e.g. during weekends, on holidays, or at night. In such an event the virus can either be harvested when at its maximum titer with personal inconvenience to employees and with increased labor cost, or it can be harvested during the next regular work period with possible loss of titer.

OBJECTS OF THE INVENTION

It is an object of the present invention to provide automated means for harvesting a virus. Another object is to provide automated means for harvesting a virus when the viral titer is at a maximum. Another object is to provide automated means for harvesting a virus without human intervention. A further object is to harvest the virus and hold it for future use with a minimal loss of titer. These and other objects of the present invention will be apparent from the following description.

SUMMARY OF THE INVENTION

After a predetermined period of incubation, the virus harvest fluid is fed from the viral growth apparatus into a freezing tank maintained at liquid nitrogen temperature. The tank is provided with an automatic liquid nitrogen control system which maintains a desired level of liquid nitrogen. After the harvest fluid is removed from the viral growth apparatus, fresh growth media is fed into the viral growth apparatus from a growth media reservoir. Sensor means in the viral growth apparatus shut off the flow of growth media when a predetermined level is reached.

DETAILED DESCRIPTION

Figure 1:
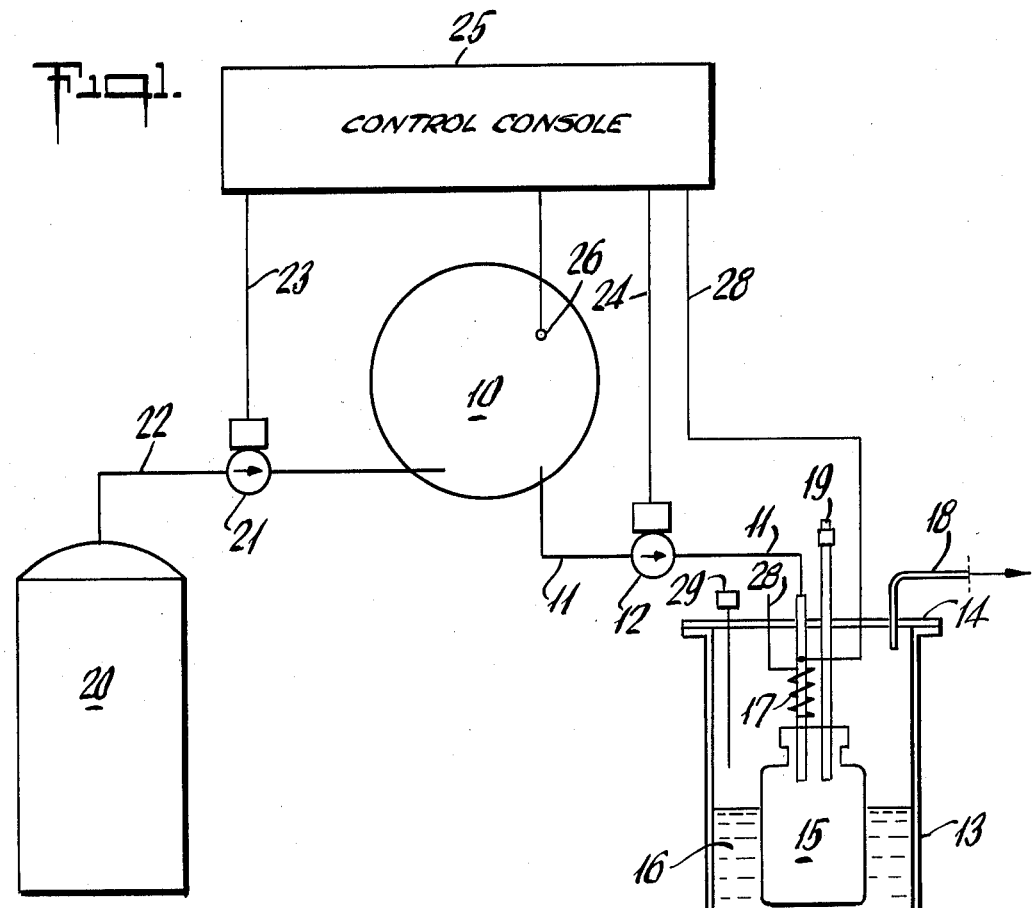
FIG. 1 is a schematic drawing of the automated virus harvesting means of the present invention.
Figure 2:
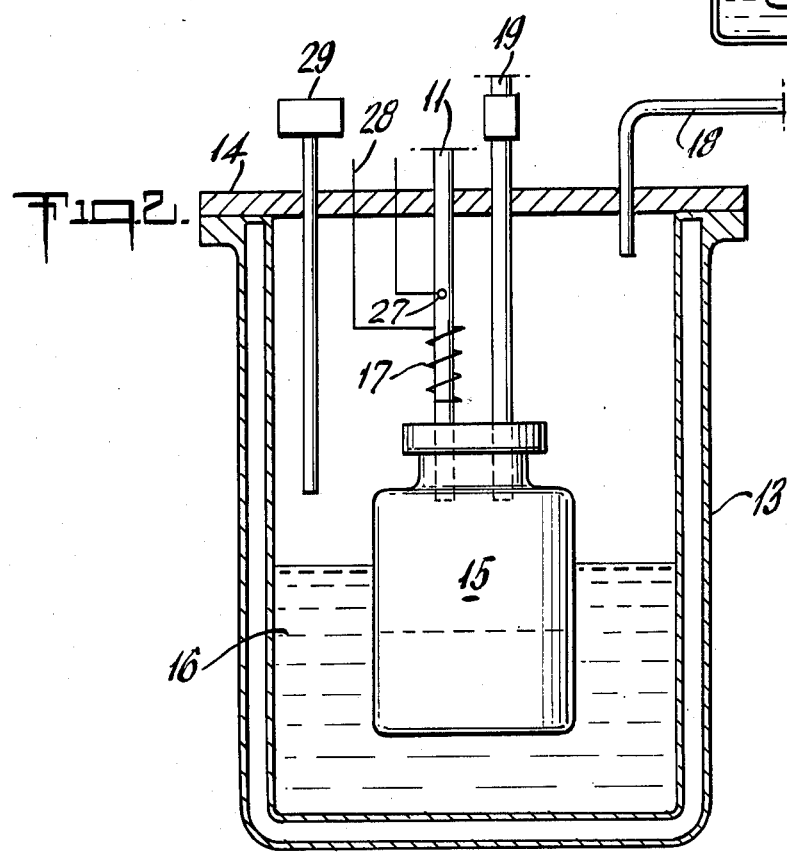
FIG. 2 is a side elevation in section of the freezing tank.

Viral growth is effected on a surface using known techniques in a viral growth tank 10. At the end of the incubation period, harvest fluid is removed from tank 10 via conduit 11 and is delivered by pump 12 to freezing tank 13. Conduit 11 passes through an opening in lid 14 of tank 13 and terminates at the mouth of container 15 which is suspended by conventional support means (not shown) in a bath 16 of liquid nitrogen. The portion of conduit 11 within tank 13 is provided with a heating coil 17 to prevent harvest fluid from freezing and blocking conduit 11. Additional openings are provided in lid 14 for passage of liquid $N_2$ inlet means 18, and of vent 19. After tank 10 has been drained, it is refilled with fresh growth media which is pumped from growth media reservoir tank 20 via pump 21 and conduit 22.

Pumps 12 and 21 are controlled by power source 23 and 24 respectively, emanating from control console 25 which drain and refill the viral growth tank at predetermined times. A level sensor 26 is provided in tank 10 to control the volume of fresh media fed from reservoir 20. A temperature sensor 27 is attached to and activates power source 28 to heating coil 17 if the temperature in conduit 11 drops to a level at which freezing may occur.

The following example illustrates the present invention without, however, limiting the same thereto.

EXAMPLE

A rotating titanium disc propagator 10 is charged with a mixture of 12 billion trypsinized duck embryo cells in Medium 199 containing 45 ml $NaHC0_3$/liter and 10% fetal calf serum. The propagator is held in the vertical postion at at temperature of 37° C. and until the cells are plated on the growth surfaces (discs). The propagator is then positioned so that the plane of the discs is in the vertical axis and a is effected. The propagator is then positioned so that the plane of the discs is in the vertical axis and a portion of the medium and serum is discharged until the unit is about half full. The discs are then rotated at a speed of 1 revolution/8 minutes and air or a mixture of 95% air and 5% $CO_2$ is passed through the unit at a rate of 100 cc/minute until the cell growth cycle has been completed at which time the spent medium is discharged from the propagator. The propagator is then recharged with 2 liters of Medium 199 containing 60 ml 2.8% $NaHCO_3$/liter, 2% α-gamma calf serum and 170 ml of a rubella virus suspension which has $-\log_{10}IND_{50}/0.1$ ml of 3.5. The unit is then set so that the discs rotate at one revolution in 8 minutes with air or a mixture of 95% air and 5% $CO_2$ passing through it at 100 cc/minute at 37° C. When the infection process has been completed the spent medium is discharged and fresh Medium 199 containing 60 ml 2.8% $NaHCO_3$/liter, 10% SPGA is added to the propagator.

Six days after seeding, the first harvest is taken. This involves removing the growth media containing the virus product and replacing it with fresh growth medium in anticipation of the next harvest which occurs in 48 hours. This is accomplished by the autoharvester and freezing apparatus. The clockwork system of the autoharvester is set to drain the tank at the appropriate time after the initial seeding of the tank with rubella virus. In this case, it is set to remove the growth fluid containing the first harvest of virus product 6 days after the initial seeding. This is carried out when the clockwork mechanism closes a switch which turns on a peristaltic pump 12 which positively drains the tank. The peristaltic pump when not in operation acts as a valve which closes off the tank. The harvest fluid is pumped into the freezing tank 13 which is maintained at liquid nitrogen temperature. A heater 17 on the inlet to the freezing tank keeps the inlet tube from freezing up and blocking the flow of liquid. The heater is controlled by a thermostat 27 which keeps it above 0° C. The tank has an automatic liquid nitrogen control system 29 which maintains the appropriate level of liquid nitrogen. In this way the harvest is immediately cooled which minimizes titer loss. At the end of the timed cycle, the pump removing fluid from the tank stops and another pump 21 of the same type moves fresh growth media from a large reservoir 20 into the viral growth tank. A level sensor 26 in the viral growth tank turns the pump off when the fresh growth media has reached the appropriate level. The foregoing procedure is then repeated at 48 hour intervals until a total of fifteen harvests have been taken.

What is claimed is:

1. In an apparatus for replicating a virus in cells growing on a surface in a viral growth tank wherein a plurality of viral harvests is removed from the viral growth tank with the cells remaining in the tank, and wherein fresh growth media is fed to the viral growth tank following each harvest except the last, the improvement comprising means for automatically removing substantially all of the viral harvest fluid from the viral growth tank at each of a predetermined plurality of times and automatically passing the fluid to a storage vessel maintained at about the temperature of liquid nitrogen and wherein at least part of the means for passing viral harvest fluid to the storage vessel is provided with means to prevent freezing of harvest fluid.

2. Apparatus according to claim 1 additionally including automatic sensor means disposed within the viral growth tank to control the quantity of fresh growth media.

3. Apparatus according to claim 2 wherein the means comprise level sensor means disposed in the viral growth tank.

4. Apparatus according to claim 1 wherein the means to prevent freezing comprise a heating coil.

5. A method of automatically harvesting a virus comprising growing a virus in cells growing on a surface in the presence of a growth medium in a viral growth propagator until the cell growth cycle is completed, automatically discharging the growth medium at predetermined times when viral titer is at a maximum, and automatically collecting the viral growth medium at about the temperature of liquid nitrogen and wherein the collecting is performed under conditions which preclude premature freezing of viral growth medium.

6. A method according to claim 5 wherein the growth medium is automatically discharged at a plurality of predetermined times and wherein fresh growth medium is added following all but the final discharge.

* * * * *